US005197895A

United States Patent [19]

Stupecky

[11] Patent Number: 5,197,895
[45] Date of Patent: Mar. 30, 1993

[54] DISPOSABLE ELECTRO-FLUIDIC CONNECTOR WITH DATA STORAGE

[75] Inventor: Josef J. Stupecky, Laguna Niguel, Calif.

[73] Assignee: Bicore Monitoring Systems, Irvine, Calif.

[21] Appl. No.: 698,589

[22] Filed: May 10, 1991

[51] Int. Cl.⁵ .......................................... H01R 13/52
[52] U.S. Cl. .................................... 439/194; 285/322;
285/921; 285/137.1; 285/119; 604/905;
604/283; 439/353
[58] Field of Search ............... 439/194, 195, 353, 409,
439/210; 285/119, 137.1, 921, 309, 312, 907,
322; 73/861.53; 604/905, 283; 128/725

[56] References Cited

U.S. PATENT DOCUMENTS

| | | | |
|---|---|---|---|
| 3,673,541 | 6/1972 | Volinskite | 439/195 |
| 3,842,389 | 10/1974 | Glover | 285/137.1 |
| 4,076,279 | 2/1978 | Klotz et al. | 285/137.1 |
| 4,214,593 | 7/1980 | Imbruce et al. | |
| 4,327,720 | 5/1982 | Bronson et al. | |
| 4,334,534 | 6/1982 | Ozaki | |
| 4,526,431 | 7/1985 | Kasukawa | 439/353 |
| 4,701,159 | 10/1987 | Brown et al. | 285/137.1 |
| 4,723,948 | 2/1988 | Clark et al. | 604/283 |
| 4,821,715 | 4/1989 | Downing | |
| 4,895,570 | 1/1990 | Larkin | 604/905 |
| 4,900,065 | 2/1990 | Houck | 285/137.1 |
| 5,047,021 | 9/1991 | Utterberg | 604/238 |
| 5,052,386 | 10/1991 | Fischer, Jr. | 285/322 |
| 5,137,524 | 8/1992 | Lynn et al. | 604/283 |

FOREIGN PATENT DOCUMENTS 183396 6/1986 European Pat. Off. ............ 604/283

Primary Examiner—Eric K. Nicholson
Attorney, Agent, or Firm—Knobbe, Martens, Olson & Bear

[57] ABSTRACT

A modular constructed connector for interconnecting with a single male and female connector a plurality of electrical lines and fluid lines while maintaining a consistent bubble-tight fluid interconnection. The modular design permits the number of fluidic and electrical connections to be varied depending upon the particular application. In one embodiment, a programmable microchip is mounted within this connector. This chip stores the response characteristics of a flow meter used, for example, as an air flow measurement device in a respiratory circuit.

16 Claims, 12 Drawing Sheets

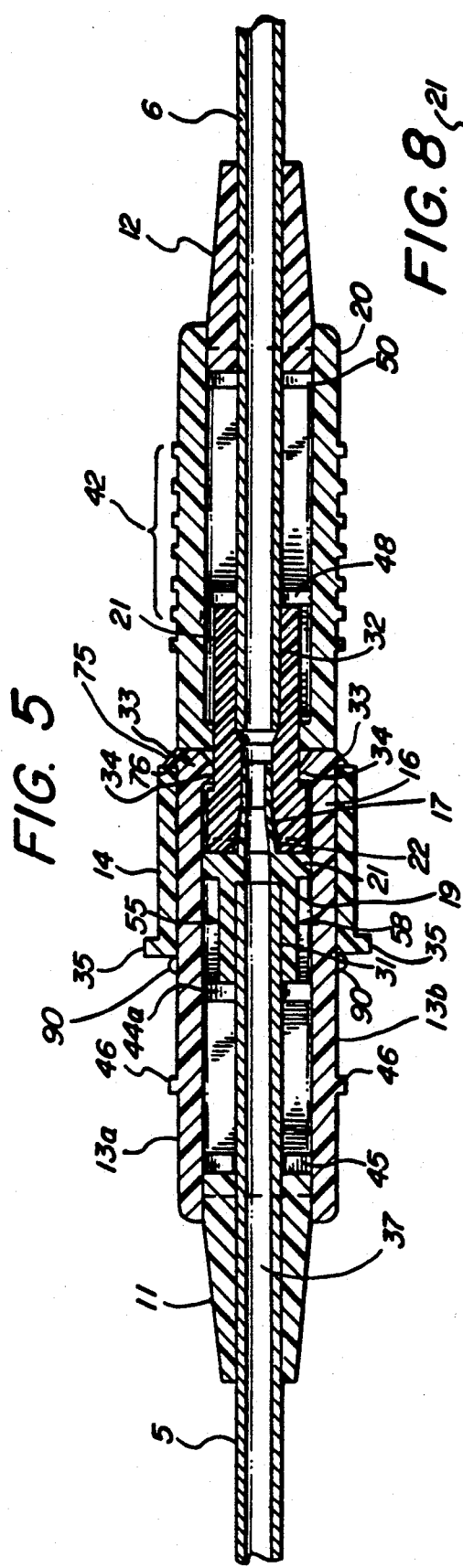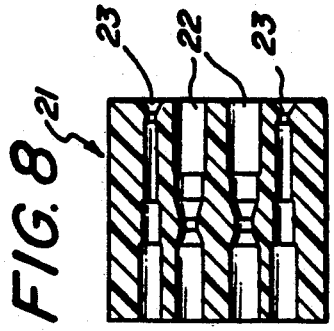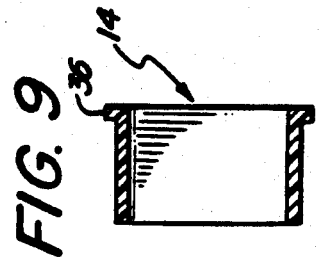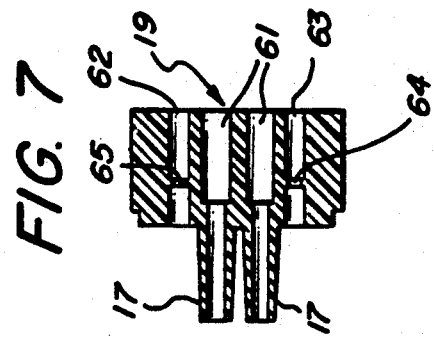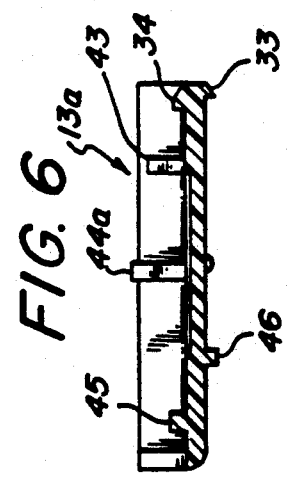

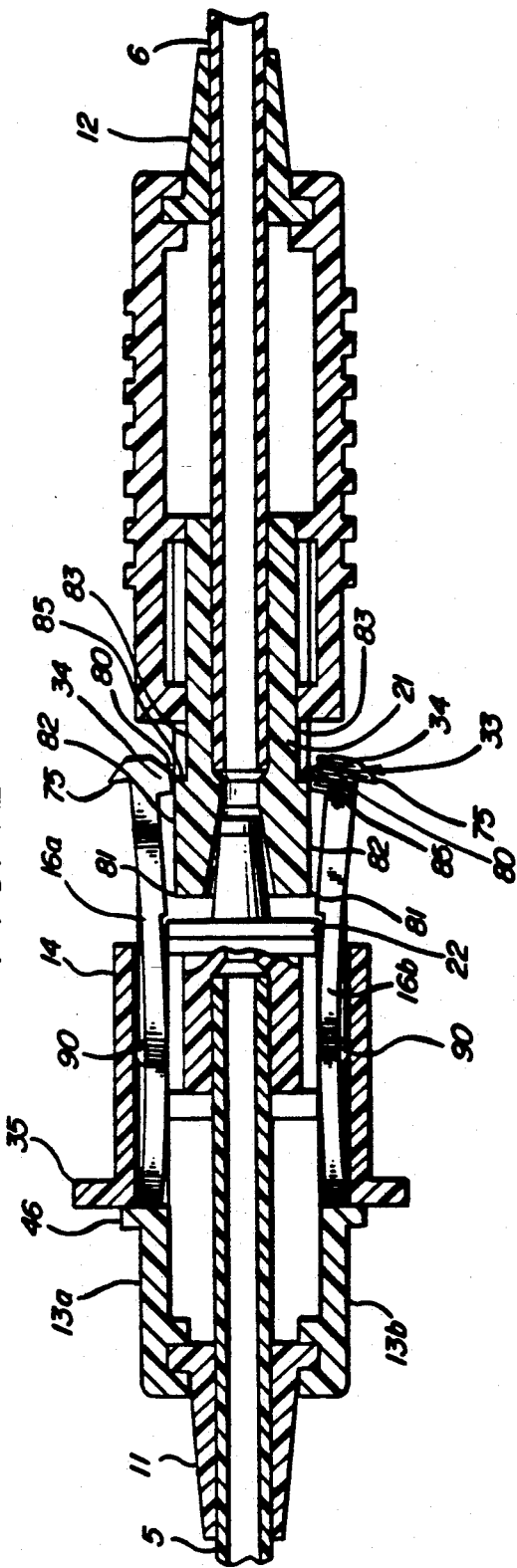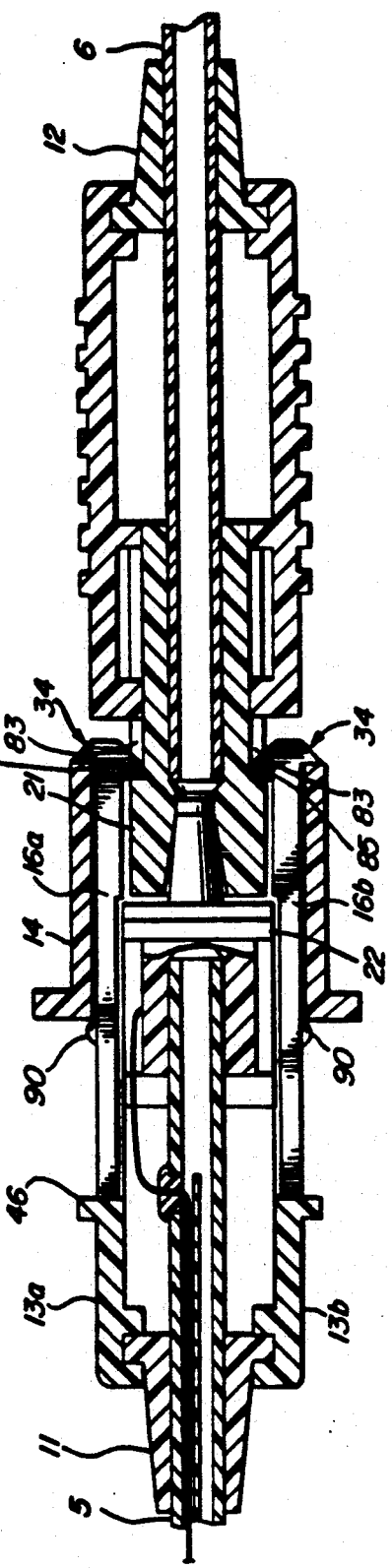

DISPOSABLE ELECTRO-FLUIDIC CONNECTOR WITH DATA STORAGE

FIELD OF THE INVENTION

The present invention relates to a low cost, disposable connector. More particularly, the present invention relates to an improved connector which reliably and rapidly connects multiple pneumatic or liquid and electric lines at the same time for use in a medical apparatus. The present invention particularly, though not exclusively, relates to medical connectors which have an electronic memory for storing the response characteristics of an in vivo sensor which is to be connected to a control apparatus via the connector.

BACKGROUND OF THE INVENTION

In the medical arts, it is often necessary to effect both pneumatic connections and electrical connections between an in vivo medical device and a control apparatus which is outside the patient's body. It can be readily appreciated that it can be time-consuming and labor-intensive for medical personnel to identify each individual fluid line and electrical lead from an in vivo device and then connect each fluid line or electrical lead to its corresponding mating part on the control apparatus.

As one example, U.S. Pat. No. 4,989,456 to Stupecky, assigned to the same assignee as the present invention, discloses a flow meter which is intended to be connected to the airway of a patient to measure the patient's air flow rate. Monitoring of respiratory air flow in critical care patients and in patients during anesthesia is very important for correctly assessing the patient's condition and for selecting the course of future treatment. In accordance with the Stupecky invention, the flow meter has two ports. Each port is placed in fluid communication with a control apparatus external to the patient for converting the pneumatic signals from the ports into an electrical signal representative of the patient's air flow. Thus, it is necessary to provide a means for connecting the flow meter to the control apparatus.

Furthermore, demand has increased in the medical industry for relatively inexpensive, disposable sensors. Disposable sensors are required to reduce the requirement for and cost of sterilization, which is necessary to reduce the risk of transmitting infectious diseases, e.g., AIDS. Unfortunately, many applications require that in vivo sensors be capable of attaining accuracies on the order of a few per cent, in order to be diagnostically useful. This means that many sensors, such as the flow meter disclosed by Stupecky, must either be made within relatively precise manufacturing tolerances to avoid the need for calibration, which makes such flow meters expensive, or must be calibrated bedside prior to each use of the flow meter, which is labor-intensive and often impractical. Under these alternatives, the cost of making or calibrating the flow meter can be prohibitive, particularly in view of the requirement that the flow meter preferably be disposable. The problem of expense in order to ensure accuracy is particularly acute in the case of flow meters.

As another example of a device which requires multiple fluid and electrical connections to a control apparatus, certain medical catheters are used for both the introduction of liquids into the body, and the measurement of pressure and temperature in different parts of the body. One such device, known as an esophageal catheter, is disclosed in U.S. Pat. No. 4,214,593, entitled "Esophageal Pressure Monitoring Device". This patent describes a balloon catheter for measurement of esophageal pressures of patients with respiratory problems. For these measurements, pneumatic lines connect an external monitoring and testing instrument to the balloon cuff positioned within the patient's stomach.

Additionally, a pH probe or a thermistor can also be advantageously mounted within the esophageal catheter so that it is inserted into the esophagus of the patient when the distal end of the catheter is located within the esophagus. Electrical wires connected to the pH probe or thermistor are connected to instruments external to the patient. In the case of a thermistor, a resistance variation of the thermistor occurs in accordance with the body temperature change of the patient and is connected by the monitoring instrument to a measurement of body temperature.

Thus, in this type of medical apparatus, it is necessary to connect both pneumatic and electrical lines from the patient's body to a monitoring instrument, in this example a cardiopulmonary monitor. Since these medical catheters are typically discarded after a single patient use, the cost of connector must be kept to a minimum without sacrificing reliability.

Further, as was the case with the flow meter discussed above, not just any pH probe or thermistor can be attached to the prior art multi-purpose catheters for providing an accurate pH or temperature indications. This is because many pH probes and thermistors, particularly inexpensive probes and thermistors, have relatively large accuracy tolerances. Consequently, relatively expensive pH probes and thermistors that do not require extensive calibration prior to use have conventionally been used on many of the multiple function catheters mentioned above.

Conventionally, separate connectors are employed for each of the plural pneumatic lumens and the electric wires. Typically, separate luer connectors are used for each pneumatic or fluidic connector, the luer connector including a male tapered tubular part which fits into a female tapered socket. These parts are locked together by rotating a threaded sleeve which is concentric with the tubing being connected. The engagement force between the two parts thus depends upon the torque exerted by the user, resulting in a wide range of engagement forces. By way of example, in the case of plastic luer fittings, the engagement of mating parts can vary by as much as 0.05 inches. Moreover, this locking sleeve can generate substantial axial force which is, in turn, magnified by the effect of the taper of the female socket.

The luer connector has several disadvantages. First, the contact pressure in the connector is determined by the strength of the operator who screwed in the connector; therefore, contact pressure is not constant and thus the contact reliability is low if insufficient torque is used. If, however, the luer connector is tightened with too much torque, it is often very difficult to later unscrew and disconnect the fluidic lines. Second, it is not easy to connect together or disconnect the luer connection since it requires a screwing in and screwing out motion. The problem is particularly exacerbated when several fluidic lines have to be connected. Third, as noted above, the luer connector is not adapted for multiple port connections with a single connector because of the high insertion forces and need for a separate locking means for each individual part. Connecting multiple parts is time consuming and tedious for the user who needs to correctly identify each individual fluidic line and connect it to its proper mating part. A mistake on the part of the user in connecting multiple fluidic lines with luer connectors renders inoperable the device being connected and possibly could be detrimental to the health of the patient. Further, conventional luer connectors are not cost effective when used with disposable medical products such as a disposable catheter.

SUMMARY OF THE INVENTION

In accordance with the present invention, a modular design of the connector facilitates multiple combinations of either cable mounted or panel mounted female sockets and male plugs. The number of fluidic and electrical connections may be varied depending upon the particular application. If desired, the connector can be associated with a particular sensor and can be provided with an electronic memory which stores the response characteristic of the sensor, for retrieval of the response characteristic by a diagnostic computer during use of the sensor. As a result, a low cost, reliable, rapidly connected and disconnected and easy to use connector for connecting both pneumatic and electric lines, and which can have an electronic memory, is disclosed.

In one aspect of the present invention, the connector comprises of a two-part shell. The shell comprises symmetrical upper and lower halves longitudinally split along an axis parallel to the connecting tubing. Two kinds of shells are described. One type of shell is used for the female connectors and the other type of shell is used for the male plug. A core member having pneumatic connectors and electric pins is mounted between and within the respective halves of the two shell members. This core member supports one or a plurality of pneumatic connectors, as well as a predetermined number of electrical connectors.

A significant feature of the present invention is that its modular design facilitates inexpensive manufacture of a reliable connector. Thus, all of the upper shell pieces are advantageously identical and all of the lower shell pieces are advantageously identical in configuration. An upper and lower outer shell piece may be used in combination with a plurality of different core members to provide a large family of connectors having the requisite number of fluidic and electrical connections as determined by the particular configuration of the core contained within the shells.

Another feature of the present invention is that a consistent, bubble tight fluidic connection is provided by tubular hollow male pins carried by the male core member. Advantageously, these pins have a thin, tapered exterior wall adopted to engage mating cylindrical openings formed in the female core member with a slight interference fit. This structure enables a predetermined, consistent, engagement force independent of the user while providing both a bubble tight fit and easily pressed together male and female connectors. A further advantage of this structure is obtained by forming the male pins with a sufficiently thin wall and long enough length to give the pins sufficient flexibility to compensate for small misalignment of the pins and mating female openings which are caused by production inaccuracies of individual parts.

A further advantage of the present invention is that, unlike the luer connections, the present invention provides a means for making fluidic connections which have a consistent predetermined depth of engagement. As a result, engagement forces between the male and female connector do not depend upon the force used to attach the two connector pieces and only a slight force is needed to attach and detach the male and female connector members.

An important feature of the present invention is that it enables the error-free connection of multiple fluidic and electrical lines. Unlike the prior art luer connectors which require the user to individually interconnect plural fluidic lines and a separate electrical plug or plugs, all of the multiple fluid lines and electrical lines are connected to the common core member and simultaneously joined when the male and female connectors are joined. Inadvertent mismating of these is prohibited by sloping a portion of the interior face of one of the male shells to key with a corresponding exterior portion of the female core to insure that the male and female connectors cannot be joined in an incorrect alignment of fluid and electrical lines.

The preferred embodiment of the invention advantageously provides a locking sleeve which provides a simple, reliable and strong locking mechanism while also performing several other functions. The sleeve holds together the two halves of the male shell together. The locking sleeve also provides sufficient tolerance such that the male core may move slightly within the these shell halves and thereby tolerate a certain amount of misalignment with respect to the mating female connector.

Lastly, this sleeve serves to releasably lock together a male and female connector. The male shell members include flexible locking leaves or jaws having an outer ridge adapted to engage a mating indentation formed in the female core. The flexible leaves are sufficiently flexible to permit easy engagement of the ridge with the indentation during coupling of a male to a female connector and easy disengagement of the ridge with the indentation during uncoupling of a male to a female connector. However, when the locking sleeve is slid forward onto the otherwise unconstrued ends of the flexible leaves, these leaves are prevented from upward movement so that the outer ridges therein are forced to remain within their corresponding indentations and lock together the male and female connectors. Simply sliding the locking sleeve back to its unlocked position permits the male and female connectors to be easily pulled apart.

The present invention further provides an embodiment of the electrical connectors which enables the use of relatively inexpensive sensors, and in particular relatively inexpensive flow meters, pH sensors, and thermistors. Such inexpensive sensors are characterized by a wide range of accuracy tolerance. Heretofore, it has not been practical to use such sensors in clinical applications due to the necessity of conducting a time-consuming calibration prior to each procedure for which the sensor is to be used. As envisioned by the present invention, each connector is permanently associated with a particular sensor, and the response characteristic of the sensor determined during the manufacturing process. This response characteristic is stored on a microchip that is mounted on the connector, for retrieval of the response characteristic by a diagnostic computer during clinical use of the sensor.

More specifically, in this further embodiment, a programmable microchip is mounted on the male core and electrically connected to one or more of the electrical pins which protrude from the male core. In accordance with the present invention, the male core can be associated with a sensor, e.g., a flow meter, or a pH sensor or thermistor that is attached to a multi-purpose catheter, and the response characteristic of the sensor stored on the microchip.

For example, when the sensor is a thermistor or pH electrode, the thermistor or pH electrode is advantageously calibrated by electrically connecting the pins of the connector to a computer. Specifically, prior to clinical use of the connector with thermistor or pH electrode, the pins of the connector are electrically attached to a calibration computer, which ascertains the response characteristics of the thermistor or electrode. When the computer has ascertained the response characteristics of the thermistor or pH electrode, the computer then stores the response characteristics in the electronic memory of the microchip.

The connector with sensor is then disengaged from the computer, packaged, and shipped to a clinical user. In the clinic, the connector is electrically attached the sensor to a diagnostic computer used in a medical establishment, and the sensor positioned within a patient's body. The sensor generates a signal which is representative of the patient's predetermined parameter. This signal is conducted through the pins of the connector to the diagnostic computer. The diagnostic computer queries the microchip to determine the response characteristics of the sensor. Based upon the response characteristics, the diagnostic computer applies a correction factor to the signal from the sensor to calculate an accurate value for the patient's predetermined parameter.

When the sensor is a flow meter, the flow meter is placed in fluid communication through the connector with an associated calibration pressure transducer. A calibration computer is electrically engaged with both the microchip and the transducer. A preselected volume of air is directed through the flow meter at a preselected rate, which causes the pressure transducer to generate an electrical output signal in response. The computer compares this output signal with the known actual air flow rate to ascertain the response characteristic of the flow meter, and then stores the response characteristic on the microchip. The sensor with male core and microchip are then disengaged from the calibration computer and pressure transducer for subsequent clinical use with a diagnostic computer and pressure transducer.

BRIEF DESCRIPTION OF THE DRAWINGS

FIG. 5 is an enlarged cross-sectional view of the male and female connectors connected together in accordance with the present invention with the locking sleeve being shown in the locked position.

FIG. 6 is a cross-sectional view of the top shell of the present invention.

FIG. 7 is a cross-sectional view of one of the embodiments of a male core constructed in accordance with the present invention.

FIG. 8 is a cross-sectional view of one of the embodiments of a female core constructed in accordance with the present invention.

FIG. 9 is a cross-sectional view of the locking sleeve constructed in accordance with the present invention.

FIG. 12 is an enlarged cross-sectional view of the male and female connectors as they are being interconnected.

FIG. 13 is an enlarged cross-sectional view of the male and female connectors connected together with the locking sleeve being shown in the locked position.

FIG. 17 is a perspective view of a female connector for attachment to the housing of an instrument or the like.

DETAILED DESCRIPTION OF THE INVENTION

A. Overall Description of the Male and Female Connectors

Figure 1:
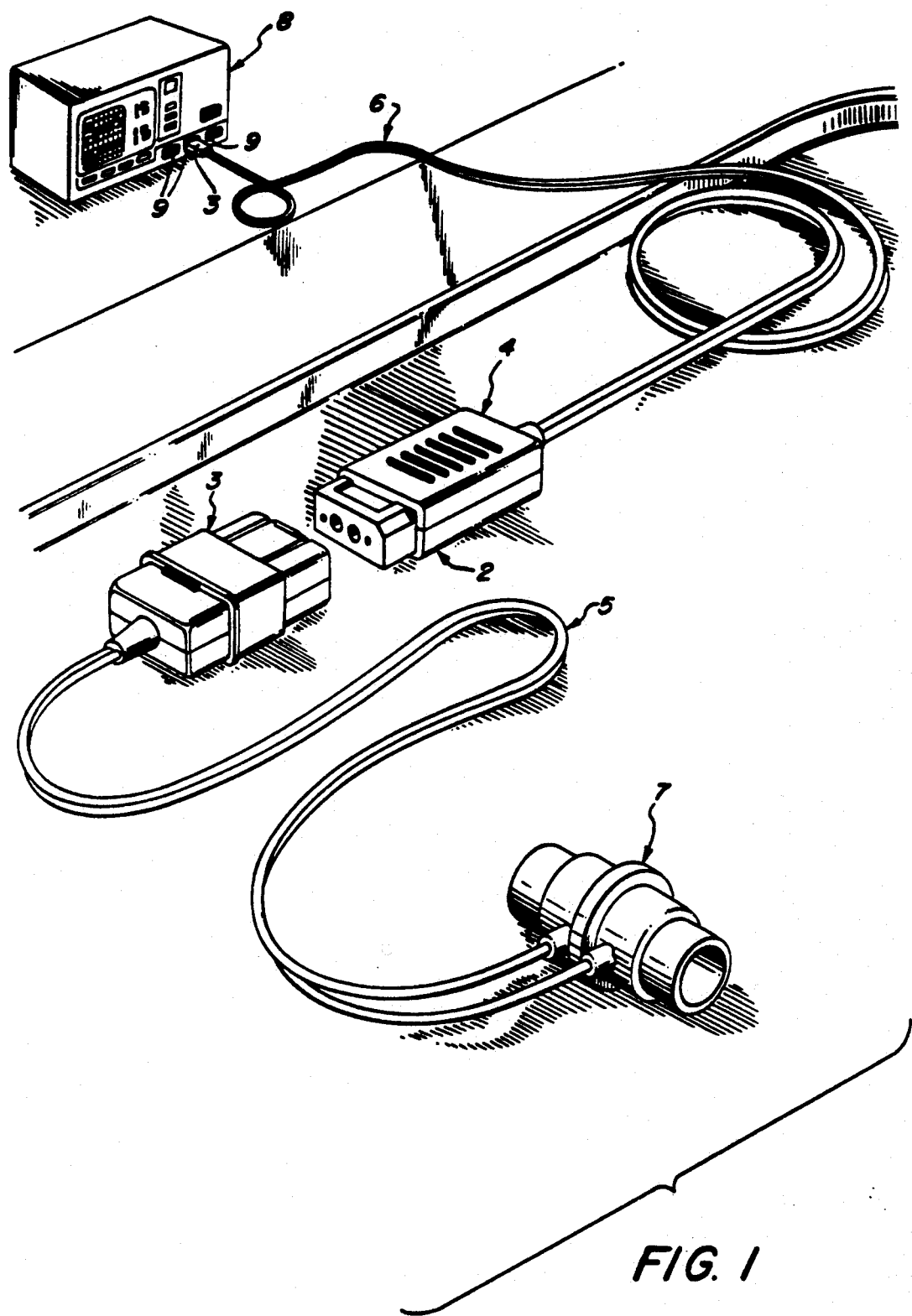
FIG. 1 is a perspective view of a male and female connector constructed in accordance with the present invention and with a medical apparatus.

FIG. 1 shows a typical example of a medical apparatus utilizing male and female connectors constructed in accordance with the present invention. The connector 2 of the present invention comprises a male receptacle connector 3 and a female receptacle connector 4. In the example shown, the male connector 3 is connected to an air flow transducer 7 through a pneumatic double-lumen tube 5. Exemplary embodiments of air flow transducer 7 are disclosed and claimed in Applicant's copending patent application, Ser. No. 432,040, filed Nov. 6, 1989 now U.S. Pat. No. 5,033,312 for "Gas Flow Meter Housing" and Applicant's U.S. Pat. No. 4,989,456 for "Variable Area Obstruction Gas Flow Meters."

A female input connector 9 affixed to the housing of instrument 8 has, advantageously, a similar structure as the female connector 4 for connection to another male connector 3 likewise constructed in accordance with the present invention. The female connector 4 is connected to a measuring and monitoring instrument 8 through a cable 6 which is comprised of both one or more pneumatic tubes or lines and one or more electric wires from the transducer 7.

In the example shown, the pneumatic electrical cable 6 provides both fluidic lines for air flow data or fluidic data to the measuring and monitoring instrument 8 and electrical lines for electric signal data to the measuring and monitoring instrument 8. The measuring and monitoring instrument 8 will typically measure and monitor air pressure, air flow rate of respiratory system.

The instrument 8 advantageously includes plural female input connectors 9. Thus, although it is not shown, one of these other connectors can be connected via pneumatic and electrical cables to a catheter, as described hereinabove with reference to U.S. Pat. No. 4,214,593 and pending U.S. patent application Ser. No. 515,370 now abandoned.

Figure 2:
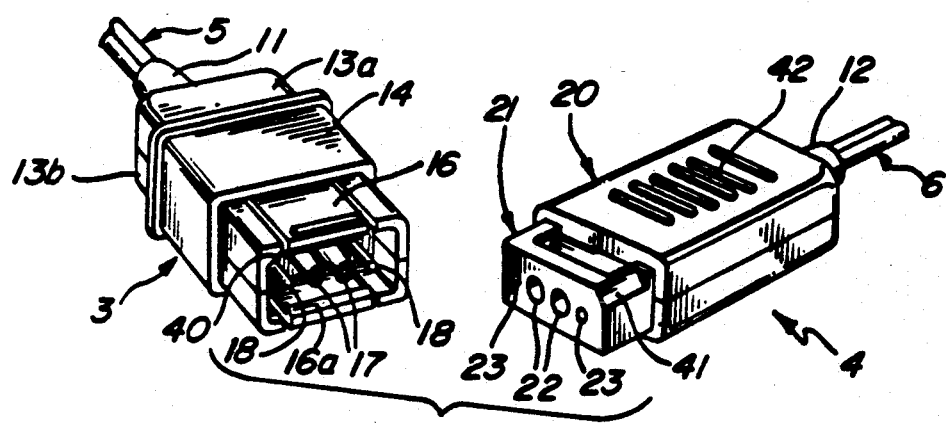
FIG. 2 is a perspective view of the male and female connectors of the present invention showing the external configuration of the electrical and fluidic contact portions of both connectors.

The outer structure of the male and female connector of the present invention is illustrated in FIG. 2. The male connector 3 is formed of an upper male shell 13a, a lower male shell 13b, a strain relief bushing 11 and a slidable locking sleeve 14. The cable 5 is advantageously a combination of pneumatic lumen and electric cables and is connected to the male connector 3 through stress relief 11. In the embodiment shown, there are provided a pair of tubular hollow pneumatic male pins 17 and a pair of electrical male pins 18.

Figure 3:
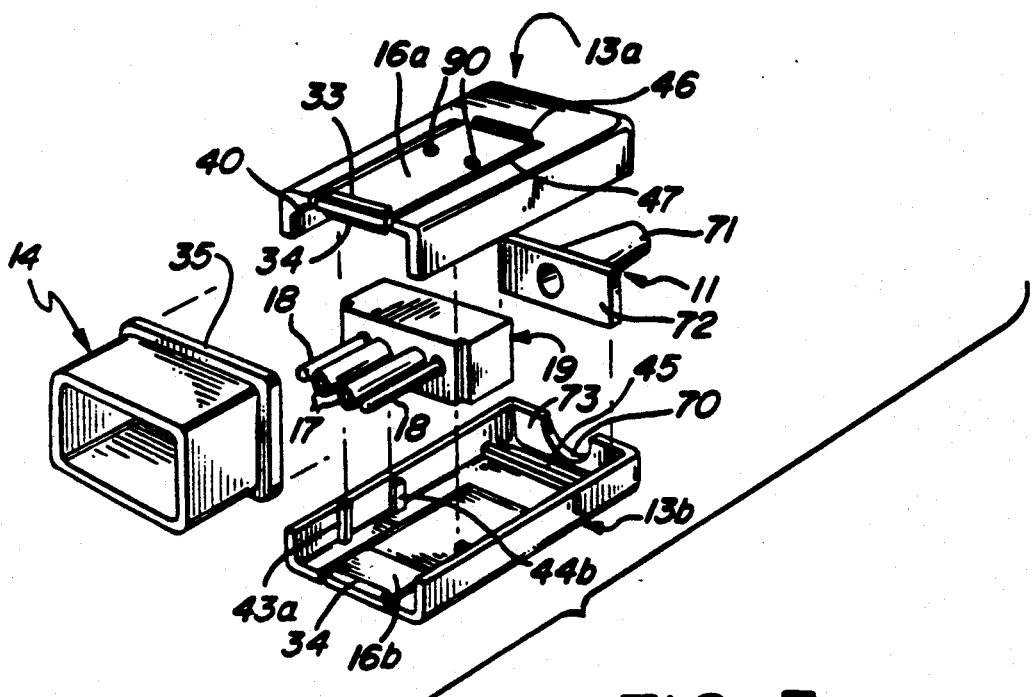
FIG. 3 is an exploded view of the male connector showing the internal configuration of an embodiment of the present invention.

Each half of the male shells 13a, 13b includes a flexible locking leaf or jaw 16 having a locking ridge 34, shown in FIG. 3, at the peripheral edge. As described below with reference to FIGS. 5, 12 and 13, this locking ridge is adopted to engage a slot in the female connector 4. The tip of the leaf 16 (and thus the ridge 34) can be slightly moved up and down due to the elasticity of the plastic material forming the male shell 13. As described in detail below, the locking sleeve 14 slidably moves over the male shell 13 to lock the connection between the male connector 3 and female connector 4 by prohibiting the up down movement of the leaf 16. A ridge 36 (FIG. 9) extends around the entire circumference of the sleeve 14 and facilitates holding onto the sleeve with the fingers of one hand so that the user may easily move it from an unlocked to locked position and from a locked to an unlocked position.

The female connector 4 is advantageously formed of a pair of female shells 20, a strain relief bushing 12 and a female core 21. The shell 20 may be identical so as to lower the cost of manufacturing the parts and assembling same. A plurality of protrusions 42 on the female shell 20 are preferably provided for eliminating slippage of the fingers when the user inserts the female connector into the male connector. The cable 6 which advantageously includes a combination of pneumatic lumen and electric conductors is connected to the female connector 4 through strain relief bushing 12. In the specific embodiment shown in FIGS. 2 and 4, this core 21 provides a pair of pneumatic female receptacles 22 and a pair of female electrical receptacles 23, respectively, corresponding to the pneumatic male pins 17 and electrical male pins 18 in the male connector 3. The female core 21 is extended from the female shells 20 so as to be inserted into the opening formed between the male shells 13a and 13b.

Mismating of the male and female connectors is prevented by forming a portion of the interior configuration of this opening to key with a corresponding exterior portion of the female core 21. Thus, referring to FIG. 2, the female core 21 has formed, at one corner, a chamfer 41 having a predetermined angle on its one corner. The male shell 13 has a triangular portion 40 which conforms with the chamfer 41 of the female core 21. Because of this combination of the chamfer 41 and the triangular portion 40, the correct position for interconnection of the male connector 3 and the female connector 4 is defined and a reverse insertion is prevented.

B. Detailed Description of the Construction and Assembly of the Male Connector

FIG. 3 shows an exploded view of the male connector 3 constructed in accordance with the present invention. The interiors of respective male shell members 13a and 13b are configured to accept and retain a male core member 19. As shown in FIGS. 3 and 7, this core 19 supports both the male tubular pneumatic pins 17 and the male electrical pins 18. In the preferred embodiment, the male pneumatic pins 17 are formed by an injection plastic mold so as to be integral with the core 19. The male electrical pins 18 are separately inserted through passages 62, 63 (FIG. 7) into the male of core 19. Annular flanges 64, 65 in the passages 62, 63 (FIG. 7) engage and hold the electrical pins 18. Referring to FIGS. 3 and 6, interior ridges 43a and 44b position the core 19 within the shells 13a and 13b. Another ridge 45 in each of the shells 13a and 13b secures in place the strain relief bushing 11.

Figure 14:
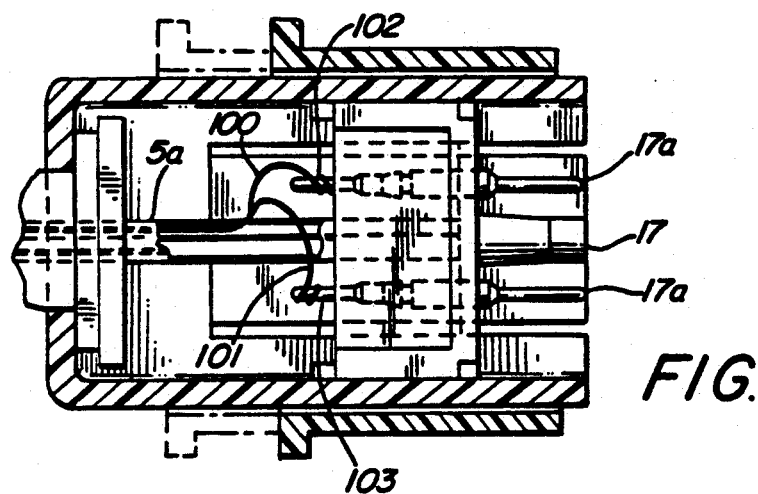
FIG. 14 is an enlarged view of a male connector core located in the lower male shell piece and showing the connection of the end of the pneumatic-electrical cable to a tubular hollow pneumatic male pin and male electrical pins.

The male connector is assembled by first inserting the end of the pneumatic-electrical cable 5 through the strain relief bushing 11. In the embodiment shown, the cable 5 includes two pneumatic tubes, the respective ends of which are inserted into receptor sockets 61 (see FIG. 7) of the male core 19 and bonded into place. An alternative embodiment of the male connector is shown in FIG. 14. In this FIGURE, the upper shell half has been removed and the cable 5a includes one pneumatic tube bonded into a single receptor socket communicating with a single male tubular pneumatic pin 17a. The cable 5a also includes a pair of electrical leads 100, 101 which are respectively soldered to the inner ends 102, 103 of a pair of male electrical contact pins 17a, 17b.

Referring back to FIG. 3, the male core 19 is then fitted between the ridges 43 and 44b of the lower half shell 13b and the strain relief 11 is fitted within its core shaped projection 71 into the semi-round cutout 70 and its rectangular base 72 between the interior ridge 45 and the end wall 73 of the shell 13b. The upper half shell 13a is then snapped over the core 19 and strain relief 11. As described below, the male shell members are semi-permanently held together by locking sleeve 14.

C. Detailed Description of the Construction and Assembly of the Female Connector The interior construction of the female connector 4 is best seen in the exploded view of FIG. 4. As described above, the upper and lower female shells 20 are identical in configuration and enclose a female core 21. The core (FIGS. 4 and 8) is generally rectangular in configuration and is enclosed by the shells within an inner chamber defined by interior ridge 48, the interior of the front wall 49 of the female shell 20, and that portion of the side wall which lies between ridge 48 and the front wall 49. The core 20 advantageously includes a released portion 55 in both its upper and lower faces (see FIGS. 4 and 5) and the resultant edge ridges 110 lie within slots 57 formed in the front face of the shells 20. The strain relief bushing 12 is positioned between the interior of the rear face of the shells 20 and interior ridge 50.

The assembly of the female connector is accomplished by passing the pneumatic-electrical cable 6 through the strain relief 12 and connecting the ends thereof to the respective pneumatic and electrical female receptacles 22, 23 carried by the female core 21. The entire female connector assembly is then snapped together and retained together by use of a suitable cement or adhesive.

D. Detailed Description of the Locking Sleeve

Locking sleeve 14 advantageously performs several functions. As shown in FIGS. 3, 5, and 12, locking sleeve 14 is forced over an upper ridge 33 formed at the peripheral end of each of the leaves 16a, 16b. This is easily accomplished since, as best shown in FIGS. 5 and 12, the outer face 75 of each of the ridges 33 is beveled so that a force perpendicular to the plane of each leaf 16 is created when the locking edge of the sleeve 14 is pushed against these beveled ridges. This perpendicular force causes the cantilever ends of the leaves 16a, 16b to move towards each other and allow the entire sleeve 14 to slip over the respective ridges 33. However, after installation, the locking sleeve is retained in position by a ridge 46 formed in the top surface of the male half shells 13 and by the ridges 33 (which present a right angle edge 76 facing the end of the sleeve 14 after it has been mounted. Thus, that distance through which the sleeve 14 may be slid upon the male connector is determined by the distance between ridge 46 and ridge 33.

The locking sleeve 14 locks together the upper and lower male shells 13a and 13b and thus provides a means to hold together these upper and lower shells without adhesive or cement while allowing the male core 19 to move slightly within the shell pieces and tolerate a certain amount of misalignment with respect to the mating female receptacle.

However, even though the sleeve 14 provides a semi-permanent retention of the members making up a male connector 3, the locking sleeve 14 can be easily removed by manually squeezing together the ends of the flexible leaves 16a, 16b so that the ridges 33 clear the inside opening of the locking sleeve.

Figure 4:
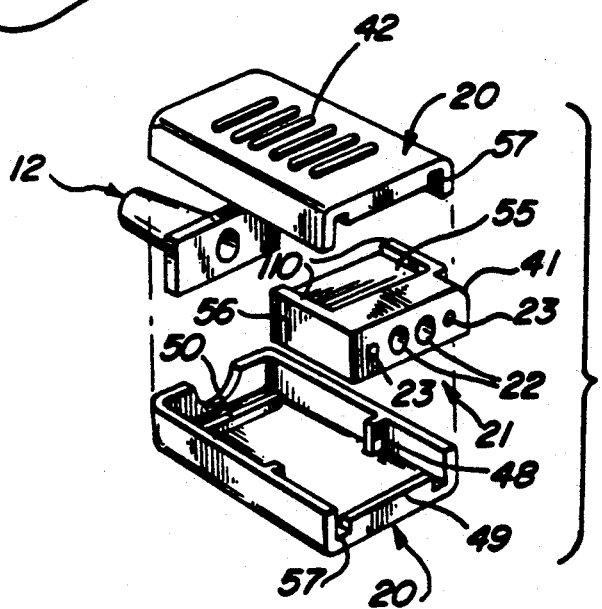
FIG. 4 is an exploded view of the female connector in accordance with the present invention.

The manner in which the locking sleeve locks together a male and female connector is best shown in FIG. 12, which illustrates a cross section of a male plug on the left being joined together with a female plug on the right and in FIGS. 5 and 13 which illustrate a cross section of the respective plugs after they have been joined together. Referring first to FIG. 12, the leading edge 80 of ridge 34 of leaves 16a and 16b is beveled so that the cantilever ends of the leaves 16a, 16b are forced apart by the front edges 81 of the female core 21. The ridges 34 then slide along the respective top and bottom surfaces 82 of the female core until the ridge drops into an indentation 83 formed in the surfaces 82 by released portion 55 in the female core 20 (FIG. 4). So long as the locking sleeve 14 is retained against ridge 46, the cantilever ends of leaves 16a, 16b are free to flex away from each other and thereby disengage their ridges 34 from the respective indentations 83 in the top and bottom of the core 20 when a moderate force is applied to pull apart the male and female connectors.

Locking together of a male and female connector is achieved by sliding the locking sleeve 14 until it abuts the ridge 33. As best shown in FIG. 13, the sleeve 14 is then held in its locked position by hemispherical bumps 90 located on the upper surfaces of the leaves 16a and 16b. The cantilevered ends of both of the leaves are then constrained from flexing away from the female core 21, and therefore the ridge 34 is "locked" against the shoulder 85 formed by the depressing of the beveled portion 55 with respect to the surface 42.

Figure 10:
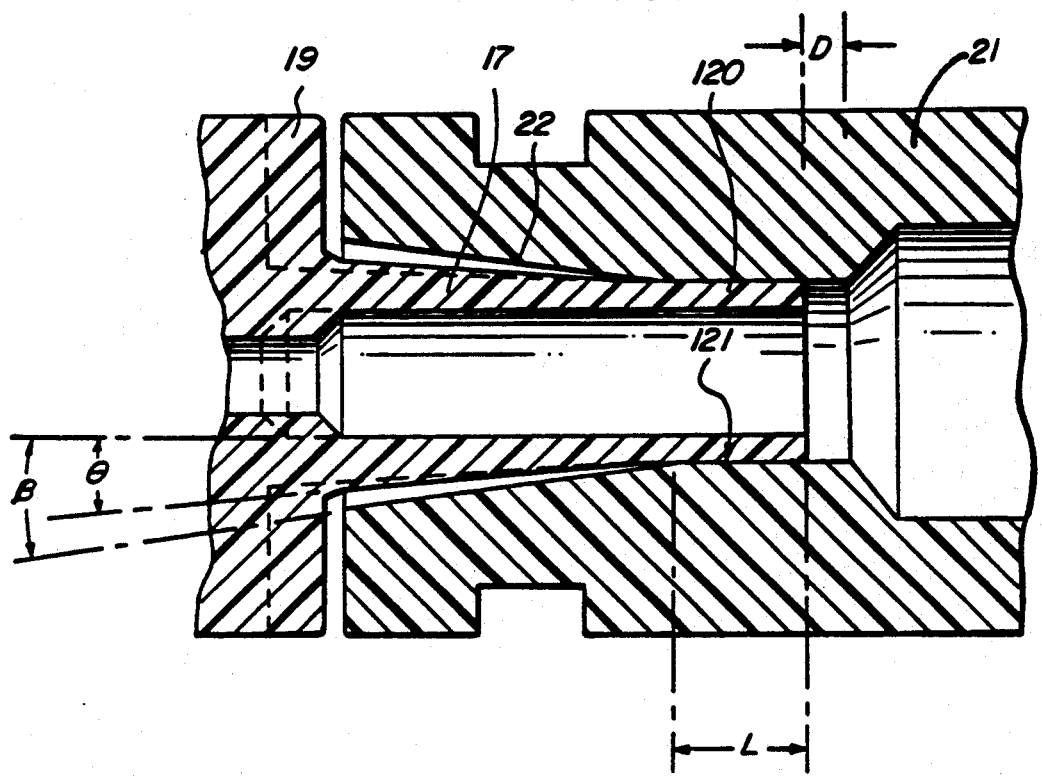
FIG. 10 is an enlarged cross-sectional view of male and female fluidic connectors constructed in accordance with the present invention.

E. Detailed Description of How the Invention Provides a Leak-Tight Interconnection A significant feature of the present invention is the manner in which a consistent leak-tight interconnection is made between plural pneumatic lines. Referring to FIG. 10, the tubular male pin 17 of the male core 19 has a predetermined taper angle $\Theta$ thereabout most of its length with the exception of the end portion L where the pin 17 changes into a cylindrical end portion 120. This cylindrical end 120 fits tightly into the female socket 22 formed in the female core 21. This socket starts with a taper angle $\beta$ greater than the taper angle $\Theta$ of the male pin. As a result, the male pin 17 is guided very easily into insertion into the mouth of the female socket 22. At the bottom end of this socket 22, its tapered portion merges into a cylindrical portion 121 in the same fashion as the male pin 17. However, the cylindrical portion 121 of this socket has a slightly smaller (typically 0.001 to 0.002 inches) internal diameter than the outer diameter of the cylindrical end portion 120 thus creating an interference fit. The end portion 121 of the pneumatic pin 17 is advantageously formed with a thin wall thickness of the radius of 0.010 inches so that the outer diameter of the plastic pin will compress to permit easy insertion thereof into the female socket 22 and provide the desired bubble tight interconnection.

F. Detailed Description of How the Invention Compensates for Inaccuracies Inherent in the Mass Production of Molded Parts Another feature of the male connector is its ability to compensate for inaccuracies inherent in mass production of molded parts. Thus, as noted above, the male core is advantageously not cemented into the male shells 13. As a result the male core 19 is slightly movable within the male shells 13 since it is not bonded to the male shells 13 with bond or adhesive. As a result, the male connector 3 tolerates some misalignment with respect to the mating female connector 4. Thus, when the male and female connectors are interconnected, the pneumatic 17 and electric pins 18 will more easily fit into the female connector 3.

Figure 15:
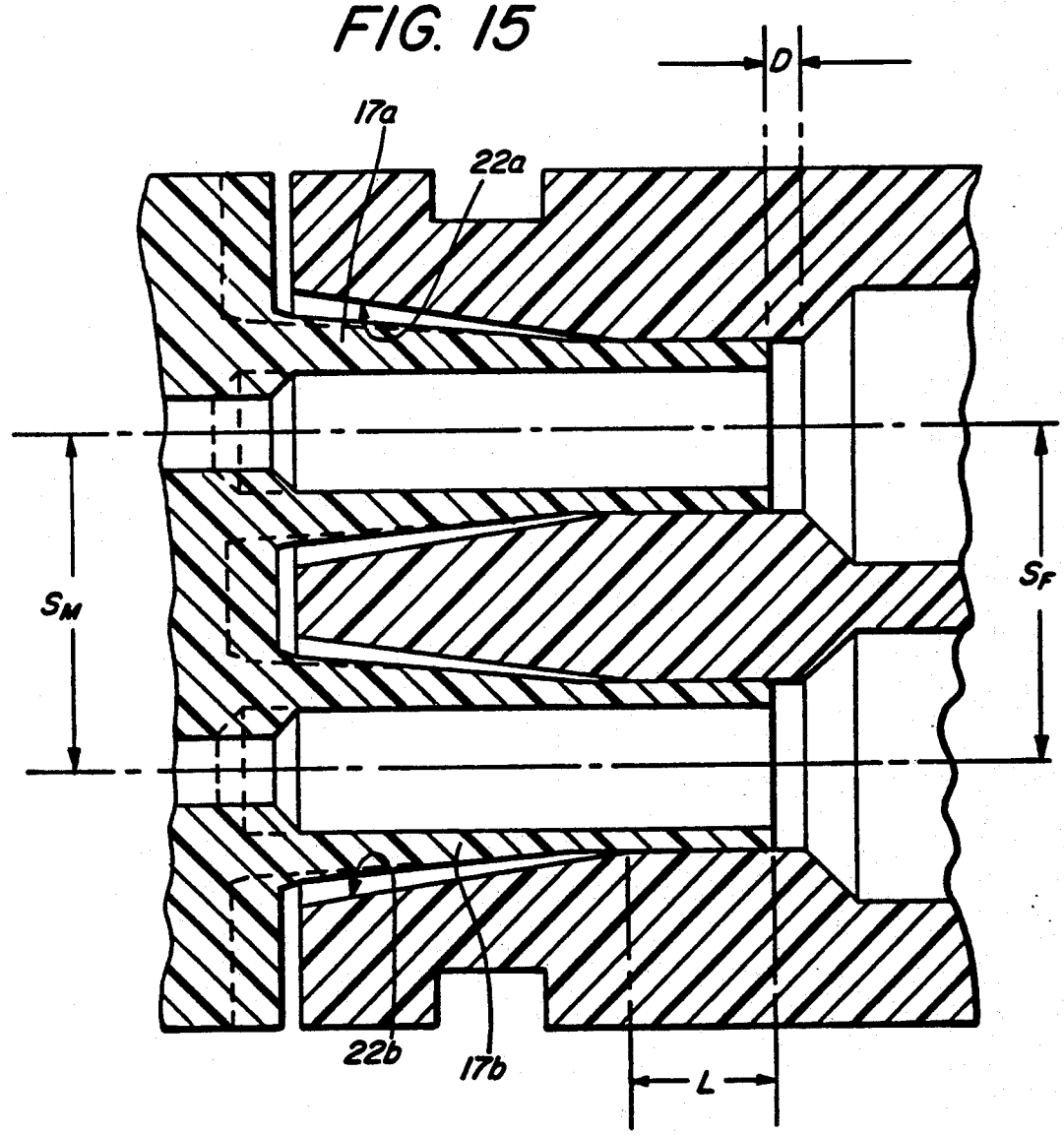
FIG. 15 is an enlargement showing the manner in which a consistent, bubble tight, fluidic connector is provided by a slight interference fit between tubular bottom male pneumatic pins and mating cylindrical openings formed in the female connector.
Figure 16:
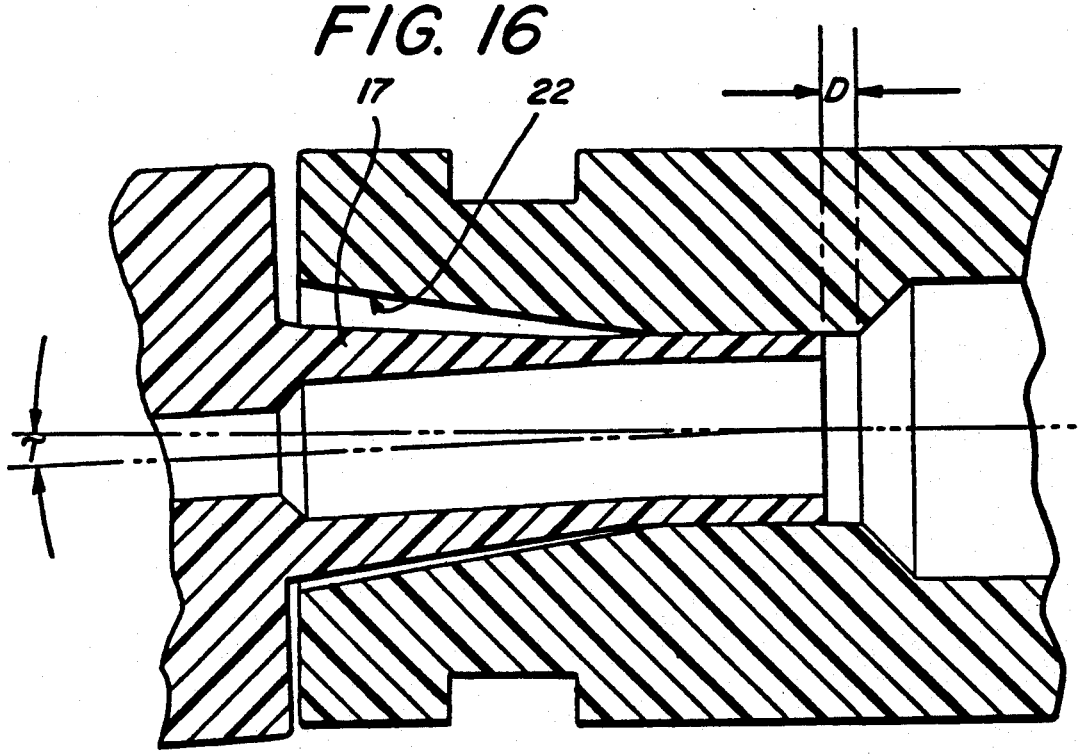
FIG. 16 is an enlargement showing in the manner in which the male pneumatic pin has sufficient flexibility to compensate for a small misalignment of the pin and the mating female opening.

In addition to the ability of the male core 19 itself to move within the male shells 13 is that the structure of the tubular male pneumatic pins 17, namely their long tapered wall, shown best in FIGS. 15 and 16, ranging typically from 0.017 down to 0.010 inches in thickness, gives these male pins 17 good flexibility so that the pins can very accurately align themselves to the female core receptacle socket 22.

The flexibility of this male pneumatic pins 17 is an important feature of the invention since it further compensates for small misalignments which are inherent in low cost manufacturing of plastic molded parts. This feature is best illustrated in the enlarged detail section of FIG. 15 showing a two-port pneumatic connection. If the center-to-center distances $S_M$ and $S_F$ for spacing of the male pins 17a, 17b and female sockets 22a, 22b are not precisely identical, the male pins 17a, 17b will bend slightly to compensate for the misalignment which maintains a leak-tight connection. The preferred amount of flexure for each is in the range of 0.005 to 0.008 inch per pin.

The fact that the sealing is accomplished by an interference fit between two cylindrical surfaces, as shown in FIGS. 10 and 15, in the area designated as "L" gives the connector a number of other significant advantages. Thus, the connector does not require a precise engagement depth for tight connection. It is sufficient if only a portion of the total length "L" of the cylindrical area is engaged and the end of the pneumatic pin 17 need not reach the bottom within the female receptacle 22. As shown in FIG. 10, there remains, after leak tight connection is established, a distance D between the end of the male pneumatic pin 17 and the bottom of the female cylinder 121 in the final receptacle 22. Distance D is typically of the order of 0.03 inches. This distance D permits extra travel of the male pin into the female receptacle to accommodate clearances and tolerances necessary for a proper function of the locking mechanism.

A further advantage of the invention, as shown in FIG. 16, is that since the faces of the male pin 17 and the female receptacle 22 do not have to be in full contact and since the female receptacle socket 22 has a larger taper angle than the flexible male pin 7, the connector can tolerate an angular misalignment $\gamma$ of several degrees without loosing a tight seal around the connections.

G. Detailed Description of a Panel Mounted Female Receptacle

Figure 17:
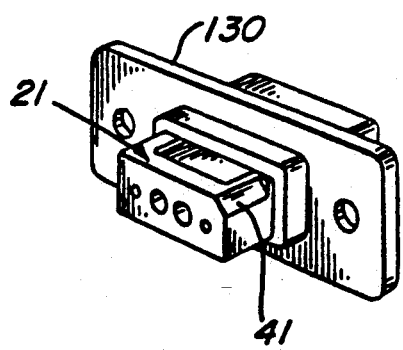
Figure 18:
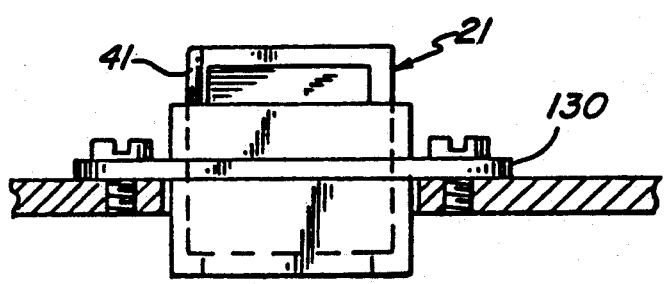
FIG. 18 is a top planar view of the female connector of FIG. 17 attached to the wall of the housing.

As described hereinabove with reference to FIG. 1, the connector of this invention can advantageously be used as a panel mounted receptacle 9. The preferred construction of this receptacle is illustrated in FIGS. 17 and 18 which illustrates a bezel 130 for receiving any female core 21 of desired configuration. The female core 21 is installed in the flanged bezel 130 and mounted to an instrument panel 40. Correct orientation of male and female parts of the connector is ensured by the indexing key 41 on the female core which matches the same shape key shown in FIG. 2.

Since these connectors are destined for throw-away type of devices and are not intended to be repaired, bonding and ultrasonic welding is used throughout for joining individual components and for tubing attachment. All components, with exception of electrical contact pins, are injection molded at minimal production cost.

Figure 11:
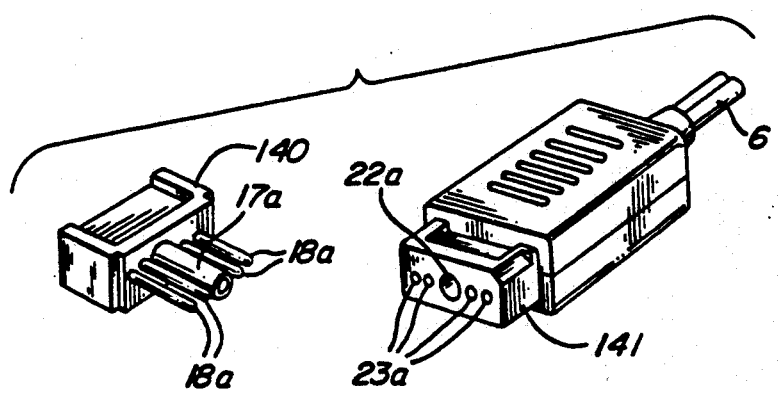
FIG. 11 is a perspective view showing an alternative embodiment of the pneumatic and electric connectors.

The modular design of the male and female connectors allows for a myriad of pneumatic-electrical combination. Thus, FIGS. 1-4 illustrate the interconnection of two pneumatic and two electrical conductors. FIG. 14 illustrates the male connector for interconnection of one pneumatic and two electrical conductors. FIG. 11 illustrates a male core 140 and female core 141 identical with the cores illustrated in FIGS. 3 and 14 and described above except that male core 140 and female core 141 provide for simultaneous interconnection of a single pneumatic line (when the male pneumatic pin 17a is inserted into the female receptacle 22a) and four electrical conductors (when the four male electrical pins 18a are inserted into the four female receptacles 23a).

H. Detailed Description of a Connector with Microchip

Figure 19:
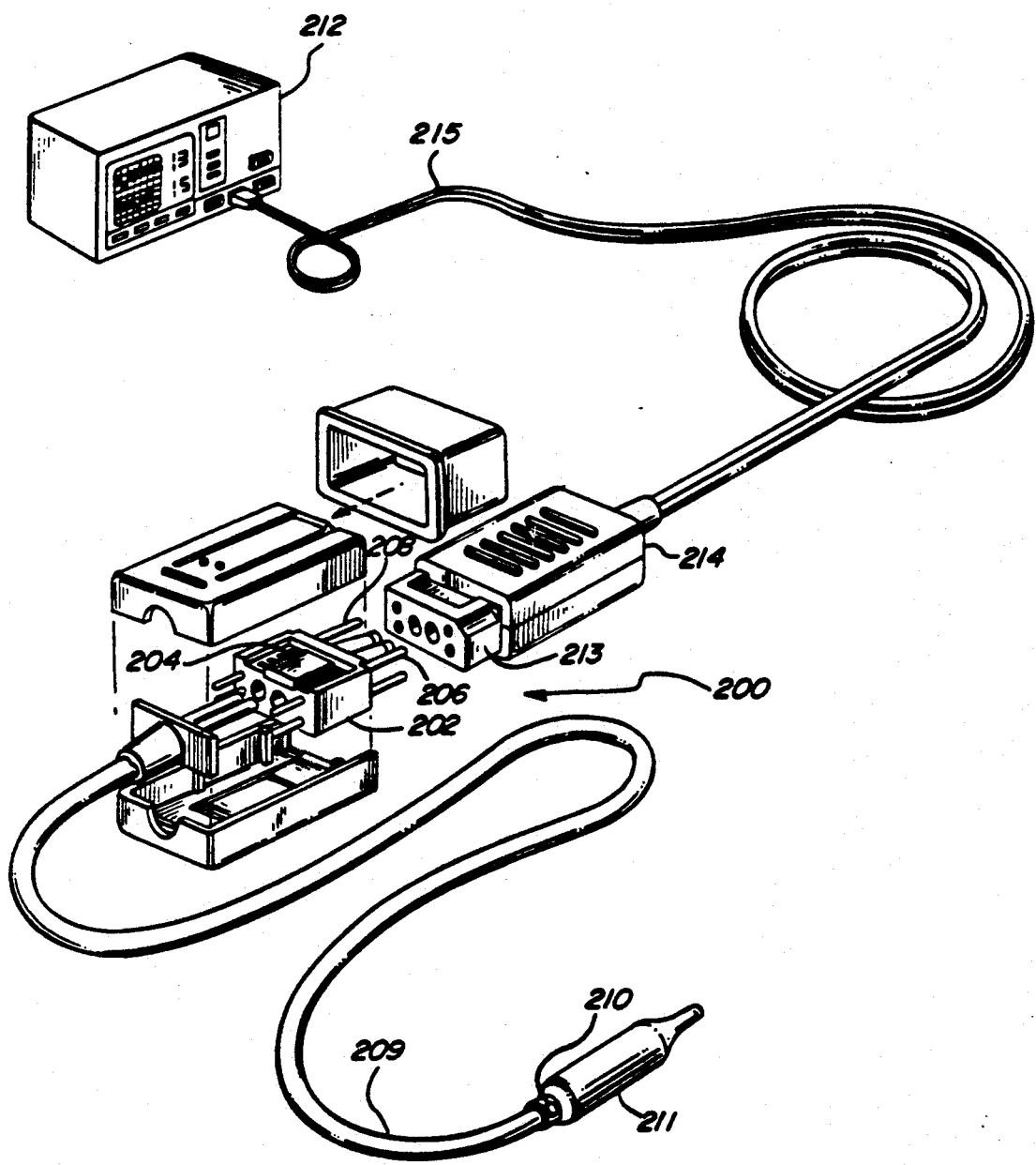
FIG. 19 is a perspective view of an alternate embodiment of the present invention in operative engagement with a multi-purpose catheter, showing the male core in an exploded view.
Figure 20:
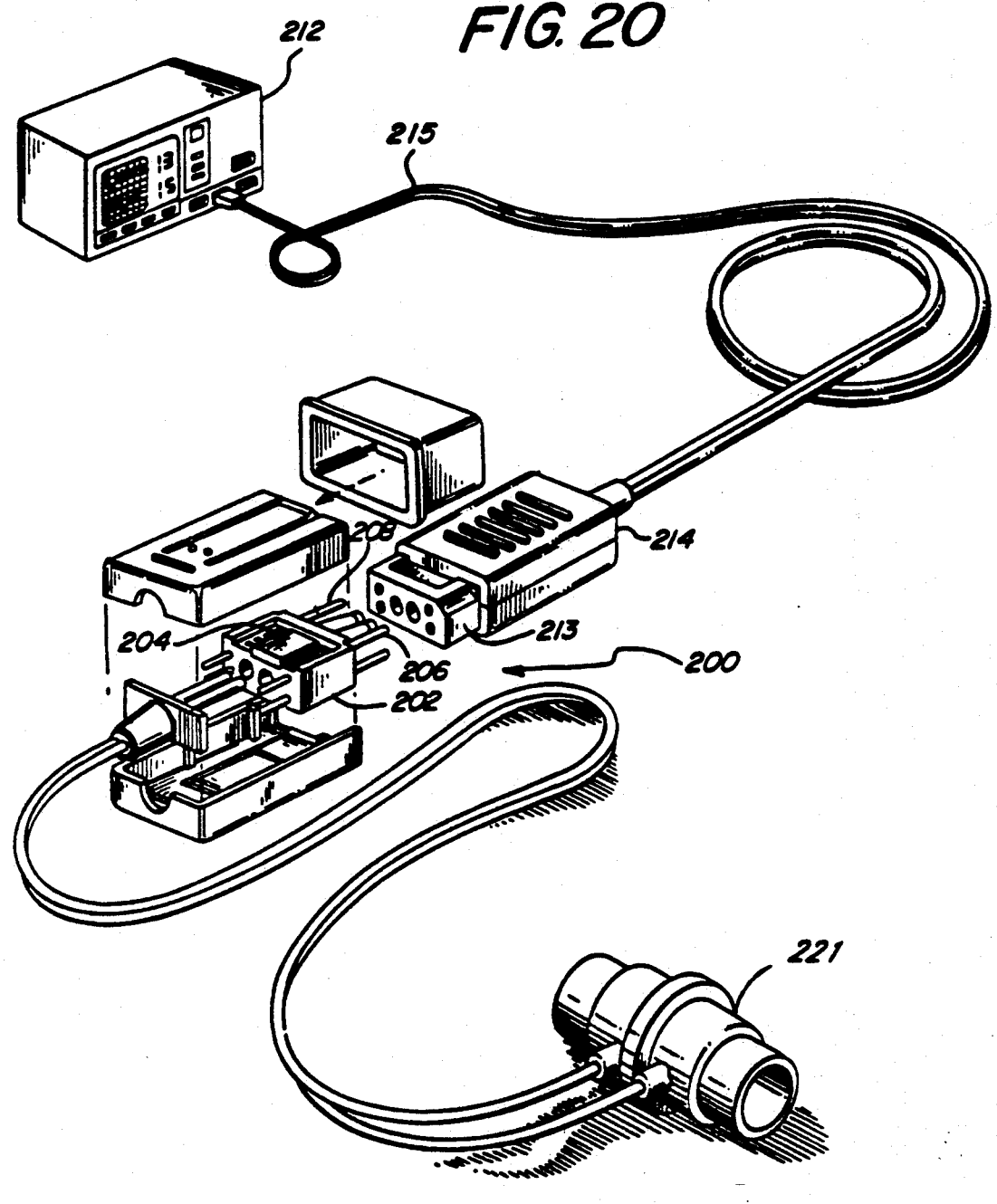
FIG. 20 is a perspective view of an alternate embodiment of the present invention in operative engagement with a flow meter, showing the male core in an exploded view.

Now referring to FIGS. 19 and 20, an alternate embodiment of the connector of the present invention is shown, generally designated 200. As shown, the connector 200 is substantially identical to the connector 2 shown in FIG. 1, with the exception that the male core 202 of the connector 200 includes an electronic microchip memory 204 which is mounted on the male core 202. The memory 204 can advantageously be solvent bonded to the male core 202. In the embodiment shown in FIGS. 19 and 20, the memory 204 is an electronically erasable programmable read-write memory (EEPROM) having a capacity of one thousand (1K) or two thousand (2K) bits of data.

As further shown in FIGS. 19 and 20, the memory 204 is electrically connected to at least two or more electrical connector pins of the male core 202. More specifically, the memory 204 is electrically connected to the electrical connector pins 206, 208 of the male core 202. Accordingly, the memory chip 204 can be located inside a connector which is attached to a sensor, such as the flow meter 221 shown in FIG. 20 or the thermistor 210 or pH sensing chip 219 of a multiple function catheter 211, shown in FIG. 19. The thermistor 210 can be any suitable temperature sensing device well-known in the art. Also, the pH sensing chip 219 can be any device suitable for in vivo sensing of the pH of a patient. The flow meter 221, shown in FIG. 20, can be the type of device disclosed in U.S. Pat. No. 4,989,456.

As shown in FIGS. 19 and 20, the memory 204 can be connected to a calibration computer 212 by attaching the female core 213 of the female receptacle connector 214 to the male core 202 and electrically connecting the computer 212 to the female core 213 via lines 215. It is to be understood that while the disclosure above discusses a memory 204 that is associated with the male core 202, the memory 204 can alternately be associated with the female core 214. It is to be further understood that sensors other than the thermistor 210 or pH sensing chip 219 can be associated with the connector 200.

Figure 21A:
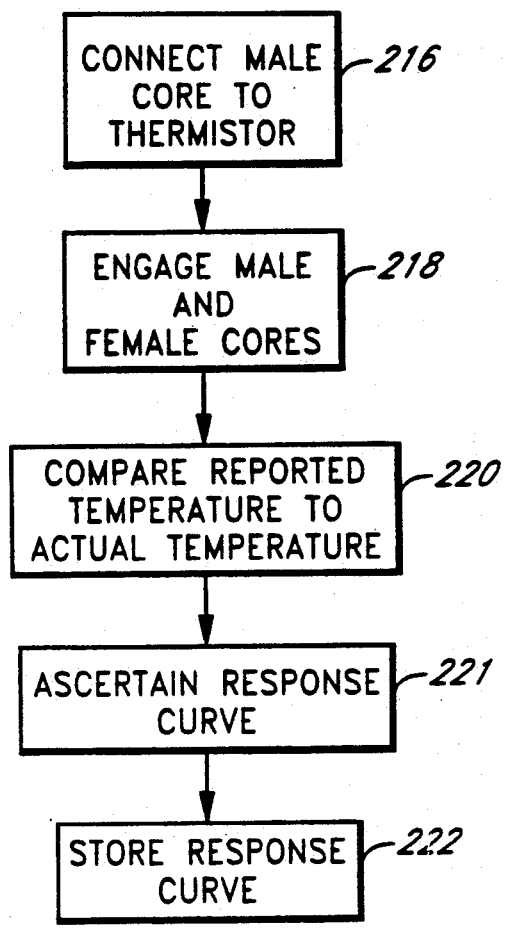
FIG. 21A is a flow chart diagram showing the sensor calibration steps of the connector shown in FIG. 19.
Figure 21B:
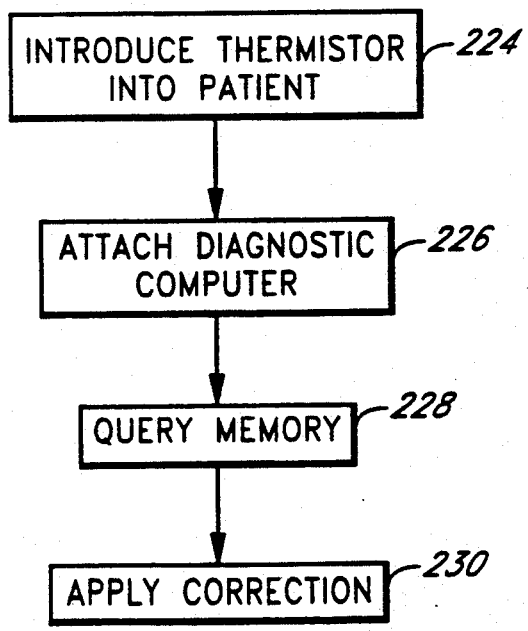
FIG. 21B is a flow chart diagram showing the sensor operation steps of the connector shown in FIG. 19.

In describing the operation of the connector 200 when the connector 200 is associated with either or both of the thermistor 210 and pH sensing chip 219, cross-reference is made to FIGS. 19, 21A, and 21B. As indicated at block 216 of FIG. 21A, taking the thermistor 210 as an example, the electrical connector pins 206, 208 of the male core 202 are electrically connected to the memory chip 204 and the thermistor 210, and the female core 213 is electrically connected to the calibration computer 212. Then, the male core 202 is engaged with the female core 213, as indicated at block 218.

In accordance with the present invention, the calibration computer 212 can be programmed to ascertain the response characteristics of the thermistor 210. More particularly, the thermistor can be placed in a test environment, the temperature and temperature variation of which is known to the calibration computer 212. The calibration computer 212 receives a signal representative of the temperature of the test environment from the thermistor 210 through the connector 200, and compares this signal with the true temperature of the test environment, as indicated at block 220. Based upon the comparison in block 220, the calibration computer 212 ascertains the response characteristics of the thermistor 210, as indicated at block 221.

As indicated at block 222, after the calibration computer 212 has ascertained the response characteristics of the thermistor 210, the computer 212 stores the response characteristics in the memory 204. If desired, additional data can be stored in the memory 204, e.g., date of sensor manufacture, sensor lot number, and sensor serial number. The female core 213 is then disengaged from the male core 202.

When it is desired to use the thermistor 210, e.g., to measure the body core temperature of a patient, the catheter 211 with thermistor 210 is introduced into the body of the patient by means well-known in the art, as indicated at block 224 of FIG. 21B. The male core 202 can be engaged with the female core 213, and the female core 213 electrically connected to a diagnostic computer (not shown), as indicated at block 226. Thus, the patient temperature signal from the thermistor 210 is conducted through the connector 200 to the diagnostic computer.

As indicated at block 228, the diagnostic computer is programmed to query the memory 204 to ascertain the response characteristics of the thermistor 210. Based upon the response characteristics of the thermistor 210, the diagnostic computer applies a correction factor to the signal from the thermistor 210, i.e., "calibrates" the signal from the thermistor 210, to determine an accurate value for the temperature of the patient. This step is indicated at block 230 in FIG. 21B.

Figure 22A:
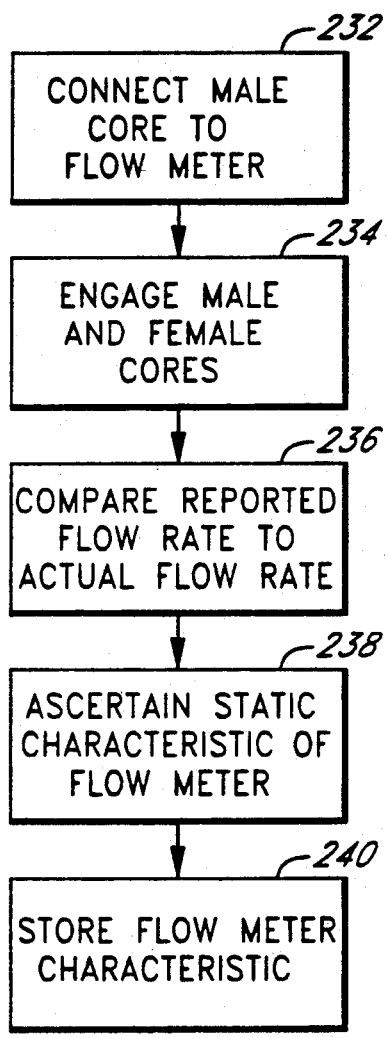
FIG. 22A is a flow chart diagram showing the sensor calibration steps of the connector shown in FIG. 20.
Figure 22B:
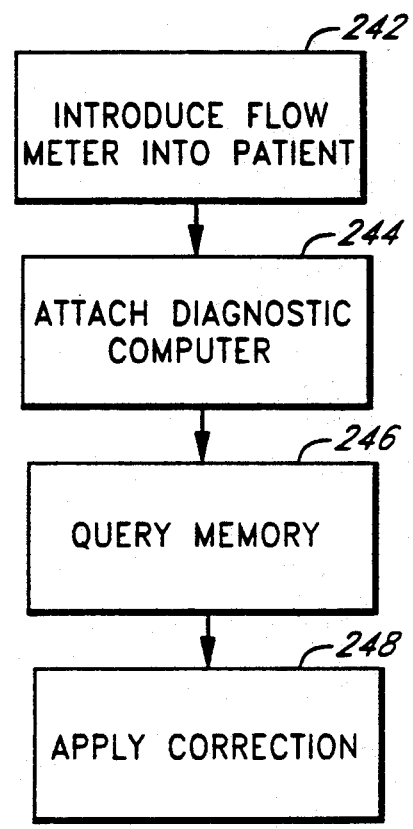
FIG. 22B is a flow chart diagram showing the sensor operation steps of the connector shown in FIG. 20.

Now referring to FIGS. 20, 22A, and 22B, the operation of the connector 200 with flow meter 221 is shown. More particularly, as indicated at block 232 in FIG. 22A, the male core is connected to the flow meter 221. Then, as indicated at block 234, the male core is connected to the female core 213. In accordance with the present invention, the female core 213 is in fluid communication with a pressure transducer that is advantageously housed with the calibration computer 212. Also, the female core 213 is electrically connected to the calibration computer 212, and the pressure transducer is electrically connected to the calibration computer 212.

Next, as indicated at block 236, a preselected volume of air is directed through the flow meter 221 at a preselected rate. The volume and flow rate of the air are known to the computer 212. In accordance with well-known principles, the pressure transducer generates an electrical signal representative of the air flow rate through the flow meter 221, as sensed by the flow meter 221. The computer 212 compares the signal from the pressure transducer with the actual air flow rate, and ascertains the response characteristic of the flow meter 221, as indicated at block 238.

As indicated at block 240, the computer 212 stores the response characteristic of the flow meter 221 in the memeory 204, along with other predetermined data, e.g., flow meter date of manufacture, lot number, and serial number. The male core 202 is then disengaged from the female core 213.

When it is desired to clinically use the flow meter 221, the flow meter 221 is introduced into a patient, as indicated at block 242 in FIG. 22B. Then, the male core 202 can be engaged with a female core (not shown), which is in turn in fluid communication with a pressure transducer (not shown) similar to the transducer discussed above and which is also electrically connected to a diagnostic computer (also not shown), as indicated at block 244.

The diagnostic computer receives the electrical signal from the transducer that is representative of the patient's air flow rate, as sensed by the flow meter 221. As indicated at block 246, the diagnostic computer queries the memory 204 to ascertain the response characteristic of the flow meter 221. Consequently, as indicated at block 248, the diagnostic computer can apply a correction factor to the signal from the pressure transducer which is representative of the response characteristic of the flow meter 204.

It is to be appreciated from the above disclosure that the connector 200 with memory 204 permits the use of a sensor having a relatively large measurement accuracy tolerance. Stated differently, the flow meter 221, pH sensing chip 219, or thermistor 210 need not be manufactured according to a comparatively precise response characteristic, because the response characteristic of each individual sensor can be ascertained and stored on the memory 204 of the male core 202 that is associated with the particular sensor, for subsequent retrieval by a diagnostic computer during use of the particular sensor.

I. Summary of Some Significant Features of the Invention

In summary, the connector design described in this patent application offers these advantages:
1. Ability to provide multiple pneumatic, electrical or both connections in one housing.
2. Very low cost, easy to assemble.
3. Very good sealing capability even under misaligned conditions.
4. Low insertion force.
5. Very simple, single motion engagement and locking.
6. Simple, reliable and strong locking mechanism.
7. Suitable for mass production.
8. Can include intelligent memory.

Although the invention has been disclosed in the context of certain preferred embodiments, it will be understood that the present invention extends beyond the specifically disclosed embodiments to other alternative embodiments of the invention. Thus it is intended that the scope of the invention should not be limited by the particularly disclosed embodiments, but should be determined by reference to the claims that follow.

I claim:

1. A multiple electrical and fluidic connector for medical apparatus for rapidly connecting and disconnecting with a single male and female connector a plurality of electrical lines and fluid lines while maintaining consistent, bubble-tight fluid interconnection thereof, said connector having a modular design so that the number of fluidic and electrical connections may be varied depending upon the particular application, said connector comprising:
   a common upper cover shell and a common lower cover shell each being substantially identical regardless of the number of electrical and fluid connections;
   a core member retained between and within said upper and lower cover shells, said core having a male configuration comprising:
      male tubular hollow fluidic pins, corresponding to the number of fluid connections, extending from the end of said core; and male electrical pins, corresponding to the number of electrical connections, extending from the end of said core, the external wall of said fluidic pins having a tapered angle throughout most of their length and merging into a cylindrical portion;

said core having a female configuration comprising:

a female fluidic receptacle having female fluidic socket openings corresponding to said male fluidic pins and female electrical socket openings corresponding to said male electrical pins, said female fluidic socket openings each having a larger circumferential opening than the cylindrical portion of said male fluidic pins, said openings tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket, said connector compensating for inaccuracies inherent in the mass production of said cores and cover shells by:

i) retention of said male core member so as to permit some slight movement of the male core within said upper and lower cover shells so as to tolerate misalignment with respect to the mating female core member;

ii) constructing said male fluidic pins so as to allow some bending thereof along their longitudinal axis so that the male pins will bend slightly to compensate for misalignment between said fluidic male pins on said male core and fluidic receptacle socket openings in said female core, and means for preventing mismating of the male and female core members by forming mating key portions in said male and female connectors to prevent an improper reverse insertion therebetween.

2. A multiple electrical and fluidic connector for medical apparatus for rapidly connecting and disconnecting with a single male and female connector a plurality of electrical lines and fluid lines while maintaining consistent, bubble-tight fluid interconnection thereof, said connector having a modular design so that the number of fluidic and electrical connections may be varied depending upon the particular application, said connector comprising:

a common upper cover shell and a common lower cover shell each being substantially identical regardless of the number of electrical and fluid connections;

a core member retained between and within said upper and lower cover shells, said core having a male configuration comprising:

male tubular hollow fluidic pins, corresponding to the number of fluid connections, extending from the end of said core; and male electrical pins, corresponding to the number of electrical connections, extending from the end of said core, the external wall of said fluidic pins having a tapered angle throughout most of their length and merging into a cylindrical portion;

said core having a female configuration comprising:

a female fluidic receptacle having female fluidic socket openings corresponding to said male fluid pins and female electrical socket openings corresponding to said male electrical pins, said female fluidic socket openings each having a larger circumferential opening than the cylindrical portion of said male fluidic pins, said openings tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket, said upper and lower shells of the male connector having respective flexible locking leaves for engagement with an abutting shoulder in the female connector, said leaves having sufficient flexibility so that when their ends are unconstrained, the respective leaves will flex apart to disengage from said shoulder, and a locking sleeve surrounding said flexible locking leaves and movable between an unlocked position remote from the respective ends of said flexible leaves and a locked position in juxtaposition with the ends of said flexible leaves to prevent flexure of said leaves so as to prevent their disengagement from said shoulder.

3. A multiple electrical and fluidic connector for medical apparatus for rapidly connecting and disconnecting with a single male and female connector a plurality of electrical lines and fluid lines while maintaining consistent, bubble-tight fluid interconnection thereof, said connector having a modular design so that the number of fluidic and electrical connections may be varied depending upon the particular application, said connector comprising:

a common upper cover shell and a common lower cover shell each being substantially identical regardless of the number of electrical and fluid connections; and a core member retained between and within said upper and lower cover shells, said core having a male configuration comprising:

male tubular hollow fluidic pins, corresponding to the number of fluid connections, extending from the end of said core; and male electrical pins, corresponding to the number of electrical connections, extending from the end of said core, the external wall of said fluidic pins having a tapered angle throughout most of their length and merging into a cylindrical portion;

said core having a female configuration comprising:

a female fluidic receptacle having female fluidic socket openings corresponding to said male fluid pins and female electrical socket openings corresponding to said male electrical pins, said female fluidic socket openings each having a larger circumferential opening than the cylindrical portion of said male fluidic pins, said openings tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket.

4. A multiple fluidic connector for medical apparatus for rapidly connecting and disconnecting with a single male and female connector a plurality of fluid lines while maintaining consistent, bubble-tight fluid interconnection thereof, said connector having a modular design so that the number of fluidic connections may be varied depending upon the particular application, said connector comprising:

a common upper cover shell and a common lower cover shell each being substantially identical regardless of the number of fluid connections;

a core member retained between and within said upper and lower cover shells, said core having a male configuration comprising:

male tubular hollow fluidic pins, corresponding to the number of fluid connections, extending from the end of said core, the external wall of said fluidic pins having a tapered angle throughout most of their length and merging into a cylindrical portion;

and said core having a female configuration comprising:

a female fluidic receptacle having female fluidic socket openings corresponding to said male fluid pins, said female fluidic socket openings each having a larger circumferential opening than the cylindrical portion of said male fluidic pins, said openings tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket, said connector compensating for inaccuracies inherent in the mass production of said cores and cover shells by:

i) retention of said male core member so as to permit some slight movement of the male core within said upper and lower cover shells so as to tolerate misalignment with respect to the mating female core member;

ii) constructing said male fluidic pins so as to allow some bending thereof along their longitudinal axis so that the male pins will bend slightly to compensate for misalignment between said fluidic male pins on said male core and fluidic receptacle socket openings in said female core, and means for preventing mismating of the male and female core members by forming mating key portions in said male and female connectors to prevent an improper reverse insertion therebetween.

5. A multiple fluidic connector for medical apparatus for rapidly connecting and disconnecting with a single male and female connector a plurality of fluid lines while maintaining consistent, bubble-tight fluid interconnection thereof, said connector having a modular design so that the number of fluidic connections may be varied depending upon the particular application, said connector comprising:

a common upper cover shell and a common lower cover shell each being substantially identical regardless of the number of fluid connections;

a core member retained between and within said upper and lower cover shells, said core having a male configuration comprising:

male tubular hollow fluidic pins, corresponding to the number of fluid connections, extending from the end of said core, the external wall of said fluidic pins having a tapered angle throughout most of their length and merging into a cylindrical portion;

and said core having a female configuration comprising:

a female fluidic receptacle having female fluidic socket openings corresponding to said male fluid pins, said female fluidic socket openings each having a larger circumferential opening than the cylindrical portion of said male fluidic pins, said openings tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket, said connector compensating for inaccuracies inherent in the mass production of said cores and cover shells by constructing said male fluidic pins so as to allow some bending thereof along their longitudinal axis so that the male pins will bend slightly to compensate for misalignment between said fluidic male pins on said male core and fluidic receptacle socket openings in said female core.

6. A multiple fluidic connector for medical apparatus for rapidly connecting and disconnecting with a single male and female connector a plurality of fluid lines while maintaining consistent, bubble-tight fluid interconnection thereof, said connector having a modular design so that the number of fluidic connections may be varied depending upon the particular application, said connector comprising:

a common upper cover shell and a common lower cover shell each being substantially identical regardless of the number of fluid connections; and a core member retained between and within said upper and lower cover shells, said core having a male configuration comprising:

male tubular hollow fluidic pins, corresponding to the number of fluid connections, extending from the end of said core, the external wall of said fluidic pins having a tapered angle throughout most of their length and merging into a cylindrical portion;

and said core having a female configuration comprising:

a female fluidic receptacle having female fluidic socket openings corresponding to said male fluid pins, said female fluidic socket openings each having a larger circumferential opening than the cylindrical portion of said male fluidic pins, said openings tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket.

7. A multiple fluidic connector for medical apparatus for rapidly connecting and disconnecting with a single male and female connector a plurality of fluid lines while maintaining consistent, bubble-tight fluid interconnection thereof, said connector having a modular design so that the number of fluidic connections may be varied depending upon the particular application, said connector comprising:
- a common upper cover shell and a common lower cover shell each being substantially identical regardless of the number of fluid connections;
- a core member retained between and within said upper and lower cover shells, said core having a male configuration comprising:
  male tubular hollow fluidic pins, corresponding to the number of fluid connections, extending from the end of said core, the external wall of said fluidic pins having a tapered angle throughout most of their length and merging into a cylindrical portion; and said core having a female configuration comprising:
  - a female fluidic receptacle having female fluidic socket openings corresponding to said male fluid pins, said female fluidic socket openings each having a larger circumferential opening than the cylindrical portion of said male fluidic pins, said openings tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket; and
- means for preventing mismating of the male and female core members by forming mating key portions in said male and female connectors to prevent an improper reverse insertion therebetween.

8. The multiple fluidic connector as described in claim 7, wherein said means for preventing mismating of the male and female connectors comprises a chamber formed at one corner of said female core and a triangular portion formed in one of said male cover members conforming to said chamber.

9. The multiple fluidic connector described in claim 7, wherein said means for preventing mismating of the male and female connectors comprises a structural member having a predetermined configuration formed on said female connector and a mating structural member on said male connector.

10. A multiple electrical and fluidic connector for medical apparatus for rapidly connecting and disconnecting with a single male and female connector a plurality of electrical lines and fluid lines while maintaining consistent, bubble-tight fluid interconnection thereof, said connector comprising:
- a common upper cover shell and a common lower cover shell each being substantially identical regardless of the number of electrical and fluid connections;
- a core member retained between and within said upper and lower cover shells, said core having a male configuration comprising:
  male tubular hollow fluidic pins, corresponding to the number of fluid connections, extending from the end of said core; and male electrical pins, corresponding to the number of electrical connections, extending from the end of said core, the external wall of said fluidic pins having a tapered angle throughout most of their length and merging into a cylindrical portion;
  and said core having a female configuration comprising:
  - a female fluidic receptacle having female fluidic socket openings corresponding to said male fluid pins and female electrical socket openings corresponding to said male electrical pins, said female fluidic socket openings each having a larger circumferential opening than the cylindrical portion of said male fluidic pins, said openings tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket; and
- a sleeve surrounding said upper and lower cover shells of said male connector, said sleeve having the dual functions of:
  i) holding together said upper and lower cover shells,
  ii) permitting some movement of the male core member between said upper and lower cover shells so as to tolerate misalignment with respect to the mating female core member, and
  iii) locking together said male and female connectors by sliding over said upper and lower cover shells from an unlock to a lock position,
- said connector further compensating for inaccuracies inherent in the mass production of said cores and cover shells by constructing said male fluidic pins so as to allow some bending thereof along their longitudinal axis so that the male pins will bend slightly to compensate for misalignment between said fluidic male pins on said male core and fluidic receptacle socket openings in said female core.

11. A multiple electrical and fluidic connector for medical apparatus for rapidly connecting and disconnecting with a single male and female connector a plurality of electrical lines and fluid lines while maintaining consistent, bubble-tight fluid interconnection thereof, said connector having a male configuration comprising:
  male tubular hollow fluidic pins, corresponding to the number of fluid connections, extending from the end of said male connector; and male electrical pins, corresponding to the number of electrical connections, extending from the end of said male connector, the external wall of said fluidic pins having a tapered angle $\theta$ throughout most of their length and merging into a cylindrical portion;
  and said connector having a female configuration comprising:
  - a female fluidic receptacle having female fluidic socket openings corresponding to said male fluid pins and female electrical socket openings corresponding to said male electrical pins, said female fluidic socket openings each having a larger circumferential opening than the cylindrical portion of said male fluidic pins, said openings tapering along an angle $\beta$ slightly larger than angle $\theta$ to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket, said connector compensating for inaccuracies inherent in the mass production of said male and female connectors by constructing said male fluidic pins so as to allow some bending thereof along their longitudinal axis so that the male pins will bend slightly to compensate for misalignment between said fluidic male pins and said fluidic female receptacle socket openings 12. A multiple connector for medical apparatus for rapidly connecting and disconnecting with a single male and female connector a plurality of fluid lines while maintaining consistent, bubble-tight fluid interconnection thereof, said connector having a male configuration comprising:

male tubular hollow fluidic pins, corresponding to the number of fluid connections, extending from the end of said male connector, the external wall of said fluidic pins having a tapered angle throughout most of their length and merging into a cylindrical portion;

and said connector having a female configuration comprising:

a female fluidic receptacle having female fluidic socket openings corresponding to said male fluid pins, said female fluidic socket tapering to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets.

13. A multiple electrical and fluidic connector for medical apparatus for rapidly connecting and disconnecting with a single male and female connector a plurality of electrical lines and fluid lines while maintaining consistent, bubble-tight fluid interconnection thereof, said connector having a modular design so that the number of fluidic and electrical connections may be varied depending upon the particular application, said connector comprising:

a common upper cover shell and a common lower cover shell each being substantially identical regardless of the number of electrical and fluid connections;

a core member retained between and within said upper and lower cover shells, said core having a male configuration comprising:

male tubular hollow fluidic pins, corresponding to the number of fluid connections, extending from the end of said core; and male electrical pins, corresponding to the number of electrical connections, extending from the end of said core, the external wall of said fluidic pins having a tapered angle throughout most of their length and merging into a cylindrical portion;

said core having a female configuration comprising:

a female fluidic receptacle having female fluidic socket openings corresponding to said male fluid pins and female electrical socket openings corresponding to said male electrical pins, said female fluidic socket openings each having a larger circumferential opening than the cylindrical portion of said male fluidic pins, said openings tapering along an angle $\beta$ slightly larger than angle $\theta$ to a narrower internal cylindrical portion having an internal diameter slightly smaller than the outer diameter of the cylindrical portion of the male fluidic pin so that an interference fluid-tight fit is created when said male fluidic tubular pins are inserted into said female receptacle fluidic sockets, without any requirement that the end of the male pin abut a seat at the bottom of a female receptacle socket, said connector compensating for inaccuracies inherent in the mass production of said cores and cover shells by:

i) retention of said male core member so as to permit some slight movement of the male core within said upper and lower cover shells so as to tolerate misalignment with respect to the mating female core member;

ii) constructing said male fluidic pins so as to allow some bending thereof along their longitudinal axis so that the male pins will bend slightly to compensate for misalignment between said fluidic male pins on said male core and fluidic receptacle socket openings in said female core, and means for preventing mismating of the male and female core members by forming mating key portions in said male and female connectors to prevent an improper reverse insertion therebetween.

14. A multiple electrical and fluidic connector for medical apparatus for rapidly connecting and disconnecting with a single male and female connector a plurality of electrical lines and fluid lines while maintaining consistent, bubble-tight fluid interconnection thereof, said connector having a modular design so that the number of fluidic and electrical connections may be varied depending upon the particular application, said connector comprising:

a common upper cover shell and a common lower cover shell each being substantially identical regardless of the number of electrical and fluid connections; and a core member retained between and within said upper and lower cover shells, said core having a male configuration comprising:

male tubular hollow fluidic pins, corresponding to the number of fluid connections, extending from the end of said core; and male electrical pins, corresponding to the number of electrical connections, extending from the end of said core, said core having a female configuration comprising:

a female fluidic receptacle having female fluidic socket openings corresponding to said male fluid pins and female electrical socket openings corresponding to said male electrical pins.

15. A multiple electrical and fluidic connector for medical apparatus for rapidly connecting and disconnecting with a single male and female connector a plurality of electrical lines and fluid lines while maintaining consistent, bubble-tight fluid interconnection thereof, said connector having a modular design so that the number of fluidic and electrical connections may be varied depending upon the particular application, said connector comprising:

a common upper cover shell and a common lower cover shell each being substantially identical regardless of the number of electrical and fluid connections;

a core member retained between and within said upper and lower cover shells, said core having a male configuration comprising:

male tubular hollow fluidic pins, corresponding to the number of fluid connections, extending from the end of said core; and male electrical pins, corresponding to the number of electrical connections, extending from the end of said core, said core having a female configuration comprising:

a female fluidic receptacle having female fluidic socket openings corresponding to said male fluid pins and female electrical socket openings corresponding to said male electrical pins; and means for selectively locking together said male and female connectors.

16. The multiple electrical and fluidic connector of claim 15, wherein said means for selectively locking together said male and female connectors comprises:

respective flexible locking leaves on said upper and lower shells of the male connector for engagement with an abutting shoulder in the female connector, said leaves having sufficient flexibility so that when their ends are unconstrained, the respective leaves will flex apart to disengage from said shoulder, and a locking sleeve surrounding said flexible locking leaves and movable between an unlocked position remote from the respective ends of said flexible leaves and a locked position in juxtaposition with the ends of said flexible leaves to prevent flexure of said leaves so as to prevent their disengagement from said shoulder.

* * * * *